(12) United States Patent
Goldstein et al.

(10) Patent No.: US 8,213,649 B2
(45) Date of Patent: Jul. 3, 2012

(54) METHOD AND DEVICE FOR EVALUATING AUDITORY HEALTH

(75) Inventors: Steven Wayne Goldstein, Delray Beach, FL (US); John Usher, Montreal (CA); Marc Andre Boillot, Plantation, FL (US)

(73) Assignee: Personics Holdings Inc., Boca Raton, FL (US)

( * ) Notice: Subject to any disclaimer, the term of this patent is extended or adjusted under 35 U.S.C. 154(b) by 1186 days.

(21) Appl. No.: 12/025,146

(22) Filed: Feb. 4, 2008

(65) Prior Publication Data

US 2008/0219486 A1 Sep. 11, 2008

Related U.S. Application Data

(60) Provisional application No. 60/887,980, filed on Feb. 2, 2007.

(51) Int. Cl.
*H04R 25/00* (2006.01)

(52) U.S. Cl. .......................................... 381/312; 381/60

(58) Field of Classification Search .................. 607/134
See application file for complete search history.

(56) References Cited

U.S. PATENT DOCUMENTS 5,594,174 A * 1/1997 Keefe .............................. 73/585
5,776,179 A 7/1998 Ren et al.

* cited by examiner

*Primary Examiner* — David Vu
*Assistant Examiner* — Jonathan Han
(74) *Attorney, Agent, or Firm* — RatnerPrestia

(57) ABSTRACT

An earpiece (100) and a method (300) for evaluating auditory health are provided. Evaluating auditory health includes embedding (302) at least one excitation signal (402) in an audio clip (404) to produce an embedded excitation signal (406), emitting (304) the embedded excitation signal to an ear canal (131) at least partially occluded by the earpiece, analyzing (312) a recorded sound field within the ear canal during a continuous delivery of the embedded excitation signal to assess auditory health, and adjusting (314) the excitation signal within the audio clip during the emitting based on comparative differences with a reference otoacoustic emission (OAE).

25 Claims, 4 Drawing Sheets

ANALYSIS 500 FIG. 5

ADJUSTMENTS 600 FIG. 6

ADJUSTMENTS 700 FIG. 7

METHOD AND DEVICE FOR EVALUATING AUDITORY HEALTH

CROSS REFERENCE TO RELATED APPLICATIONS

This application is a Non-Provisional Application of and claims the priority benefit of Provisional Application No. 60/887,980 filed on Feb. 2, 2007, the entire disclosure of which is incorporated herein by reference.

FIELD

The present invention pertains to hearing assessment using earphones, and more particularly, to a device and method for evaluating auditory health by measuring otoacoustic emissions from an eardrum.

BACKGROUND

An otoacoustic emission (OAE) is a sound which is generated from within the inner ear. Research indicates that the OAE arises from within the inner ear by a number of different cellular mechanisms. There are two types of otoacoustic emissions: Spontaneous Otoacoustic Emissions (SOAEs) and Evoked Otoacoustic Emissions (EOAEs). SOAEs arise spontaneously and EOAEs require an evoking stimulus.

OAEs are considered to be related to amplification functions of the cochlea; the organ in the ear responsible for hearing. In the absence of external stimulation applied to the cochlea, the activity of the cochlear amplification increases, leading to the production of sound. Research indicates that outer hair cells are the elements that enhance cochlear sensitivity and frequency selectivity in humans.

An otoacoustic emission test (OAE) measures an acoustic response that is produced by the inner ear (cochlea), which in essence reflects back out of the ear in response to a sound stimulus. Generally an audiologist performs the OAE test to determine a strength of the OAE and the sound stimuli that yield the OAE.

The OAE test is usually performed at an audiologist's office or a medical center under controlled conditions at appointed times. A sound probe transmits sound stimuli within the user's ear canal that may be audibly annoying and unpleasant. The results of the OAE test can also differ depending on the user's sound exposure prior to the appointed OAE test time.

A need therefore can be appreciated for evaluating a user's auditory health conveniently over time and with minimal annoyance.

SUMMARY

Embodiments in accordance with the present invention provide a method and device for evaluating auditory health.

In a first embodiment, a method for evaluating auditory health can include the steps of embedding at least one excitation signal in an audio clip to produce an embedded excitation signal, emitting the embedded excitation signal to an ear canal, and recording a sound field in the ear canal to generate a recorded sound field. The sound field can include an otoacoustic emission from an eardrum and audio content from an audio clip. The excitation signal can be at least one among a click, a pulse, or a sinc function. The embedded excitation signal can be an audio clip comprising at least one among tones, music and speech.

The method can include analyzing the recorded sound field during the step of emitting to assess auditory health, and adjusting the excitation signal based on the auditory health. In one arrangement, the excitation signal can be embedded in a masked region of the audio clip. Multiple excitation signals with differing frequencies and durations can be embedded at various time locations within the audio clip. The step of analyzing can include filtering the recorded sound field to compensate for a transducer frequency response to produce a filtered signal, and comparing the filtered signal to a reference OAE response. The step of adjusting the excitation signal can include modifying an amplitude and a frequency of the excitation signal and the audio clip.

In a second embodiment, a method for evaluating auditory health can include embedding at least one excitation signal in an audio clip to produce an embedded excitation signal, emitting the embedded excitation signal to an ear canal at least partially occluded by an earpiece, and analyzing a recorded sound field within the ear canal during continuous delivery of the embedded excitation signal to assess auditory health, and adjusting a mixing of the excitation signal with the audio clip during the emitting based on comparative differences with a reference OAE.

In a third embodiment, a method for personalized hearing evaluation can include detecting a change in an internal sound level within an ear canal at least partially occluded by an earpiece, embedding at least one excitation signal in an audio clip to produce an embedded excitation signal delivered to the ear canal responsive to detecting the change, emitting the embedded excitation signal to an ear canal, and recording a sound field in the ear canal responsive to the step of emitting to generate a recorded sound field. Responsive to an event, the sound field in the ear canal can be recorded to generate the recorded sound field. The event can be at least one among a scheduled time period, a remote event, and a user event. The event can also be triggered responsive to detecting a change in location, a change in acceleration, or a volume increase of audio content presented to the ear canal. The method can further include analyzing the recorded sound field responsive to the event to assess auditory health, and adjusting the excitation signal based on the auditory health.

In a fourth embodiment, an earpiece at least partially occluding an ear canal can include an Ear Canal Receiver (ECR) to deliver audio to the ear canal, an Ear Canal Microphone (ECM) to capture internal sound in the ear canal, and a processor operatively coupled to the ECR and ECM to embed at least one excitation signal in an audio clip to produce an embedded excitation signal, emit the embedded excitation signal to an ear canal via the ECR, and record a sound field in the ear canal via the ECM responsive to the step of emitting to generate a recorded sound field. The earpiece can include a memory to store the recorded sound field. In another configuration, the processor can record an ambient sound captured from an Ambient Sound Microphone (ASM) with the sound field.

In one aspect, the processor can detect a change in the internal sound level and embed at least one more excitation signal in the audio clip responsive to detecting the change. The processor can analyze the recorded sound field to assess auditory health responsive to an event, and adjust the excitation signal based on the auditory health. For instance, the processor can embed the excitation signal in a masked region of an audio clip, or embed multiple excitation signals with differing frequencies and durations at various time locations within the audio clip.

In a fifth embodiment, a system for monitoring auditory health can include an earpiece, a remote processor, and a memory to store a recorded sound field. The earpiece can include an Ear Canal Receiver (ECR) to deliver audio to the ear canal, an Ear Canal Microphone (ECM) to capture internal sound in the ear canal, and a transceiver operatively coupled to the ECR and the ECM to transmit and receive the audio and the internal sound. The remote processor can be communicatively coupled and external to the earpiece to embed at least one excitation signal in an audio clip to produce an embedded excitation signal, emit the embedded excitation signal to an ear canal using the ECR via the transceiver; and record a sound field in the ear canal using the ECM via the transceiver responsive to the step of emitting to generate a recorded sound field. The transceiver can transmit and send data in a compressed data format over at least one among a wired or wireless communication channel.

The remote processor can analyze the recorded sound field to assess auditory health responsive to an event, and adjust the excitation signal based on the auditory health. For instance, the remote processor can embed the OAE signal in a masked region of the audio clip. The remote processor can schedule the emitting of the excitation signal responsive to detecting a change in location of the earpiece, or a change in acceleration of the earpiece.

DETAILED DESCRIPTION

The following description of at least one exemplary embodiment is merely illustrative in nature and is in no way intended to limit the invention, its application, or uses.

Processes, techniques, apparatus, and materials as known by one of ordinary skill in the relevant art may not be discussed in detail but are intended to be part of the enabling description where appropriate, for example the fabrication and use of transducers.

In all of the examples illustrated and discussed herein, any specific values, for example the sound pressure level change, should be interpreted to be illustrative only and non-limiting. Thus, other examples of the exemplary embodiments could have different values.

Note that similar reference numerals and letters refer to similar items in the following figures, and thus once an item is defined in one figure, it may not be discussed for following figures.

Note that herein when referring to correcting or preventing an error or damage (e.g., hearing damage), a reduction of the damage or error and/or a correction of the damage or error are intended.

Figure 1:
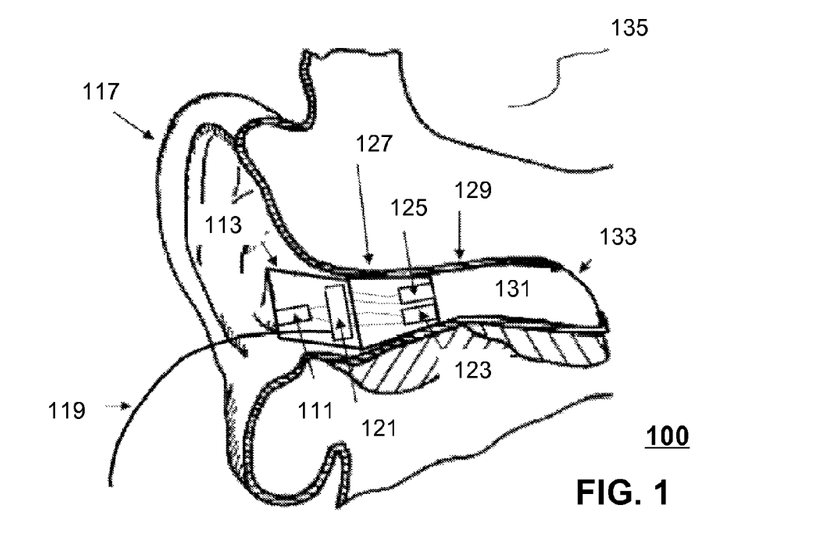
FIG. 1 is a pictorial diagram of an earpiece in accordance with an exemplary embodiment.

At least one exemplary embodiment of the invention is directed to an earpiece for ambient sound monitoring and warning detection. Reference is made to FIG. 1 in which an earpiece device, generally indicated as earpiece 100, is constructed and operates in accordance with at least one exemplary embodiment of the invention. As illustrated, earpiece 100 depicts an electro-acoustical assembly 113 for an in-the-ear acoustic assembly, as it would typically be placed in the ear canal 131 of a user 135. The earpiece 100 can be an in-the-ear earpiece, behind the ear earpiece, receiver in the ear, open-fit device, or any other suitable earpiece type. The earpiece 100 can be partially or fully occluded in the ear canal, and is suitable for use with users having healthy or abnormal auditory functioning.

Earpiece 100 includes an Ambient Sound Microphone (ASM) 111 to capture ambient sound, an Ear Canal Receiver (ECR) 125 to deliver audio to an ear canal 131, and an Ear Canal Microphone (ECM) 123 to assess a sound exposure level within the ear canal. The earpiece 100 can partially or fully occlude the ear canal 131 to provide various degrees of acoustic isolation. The assembly is designed to be inserted into the user's ear canal 131, and to form an acoustic seal with the walls 129 of the ear canal at a location 127 between the entrance 117 to the ear canal and the tympanic membrane (or ear drum) 133. Such a seal is typically achieved by means of a soft and compliant housing of assembly 113. Such a seal creates a closed cavity 131 of approximately 5 cc between the in-ear assembly 113 and the tympanic membrane 133. As a result of this seal, the ECR (speaker) 125 is able to generate a full range bass response when reproducing sounds for the user. This seal also serves to significantly reduce the sound pressure level at the user's eardrum resulting from the sound field at the entrance to the ear canal 131. This seal is also a basis for a sound isolating performance of the electro-acoustic assembly.

Located adjacent to the ECR 125, is the ECM 123, which is acoustically coupled to the (closed) ear canal cavity 131. One of its functions is that of measuring the sound pressure level in the ear canal cavity 131 as a part of testing the hearing acuity of the user as well as confirming the integrity of the acoustic seal and the working condition of the earpiece 100. In one arrangement, the ASM 111 can be housed in the assembly 113 to monitor sound pressure at the entrance to the occluded or partially occluded ear canal. All transducers shown can receive or transmit audio signals to a processor 121 that undertakes audio signal processing and provides a transceiver for audio via the wired or wireless communication path 119.

Briefly, the earpiece 100 can actively monitor a sound pressure level both inside and outside an ear canal and enhance spatial and timbral sound quality while maintaining supervision to ensure safes sound reproduction levels. The earpiece 100 in various embodiments can conduct listening tests, filter sounds in the environment, monitor warning sounds in the environment, present notification based on identified warning sounds, maintain constant audio content to ambient sound levels, and filter sound in accordance with a Personalized Hearing Level (PHL).

The earpiece 100 can generate an Ear Canal Transfer Function (ECTF) to model the ear canal 131 using ECR 125 and ECM 123, as well as an Outer Ear Canal Transfer function (OETF) using ASM 111. For instance, the ECR can deliver an impulse within the ear canal and generate the ECTF via cross correlation of the impulse with the impulse response of the ear canal. The earpiece 100 can also determine a sealing profile with the user's ear to compensate for any leakage. It also includes a Sound Pressure Level Dosimeter to estimate sound exposure and recovery times. This permits the earpiece 100 to safely administer and monitor sound exposure to the ear.

Figure 2:
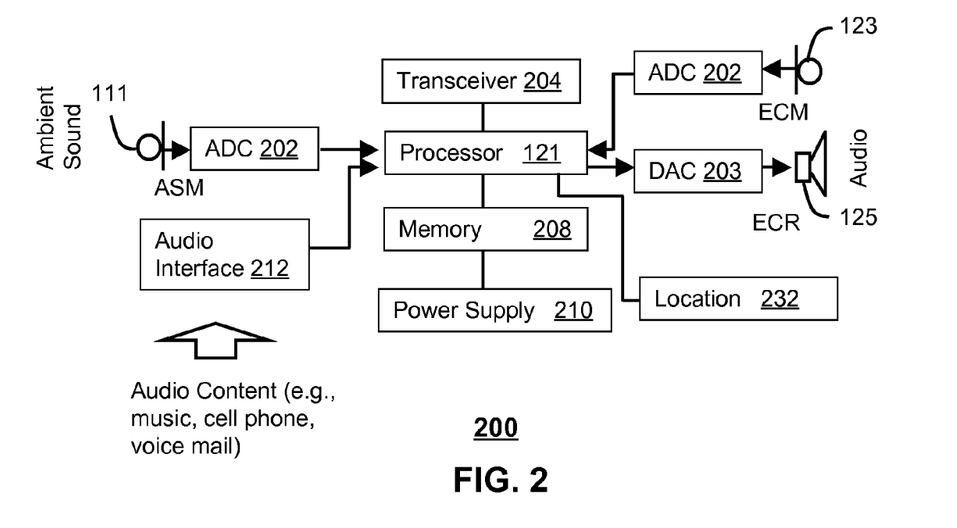
FIG. 2 is a block diagram of the earpiece in accordance with an exemplary embodiment.

Referring to FIG. 2, a block diagram 200 of the earpiece 100 in accordance with an exemplary embodiment is shown. As illustrated, the earpiece 100 can include the processor 121 operatively coupled to the ASM 111, ECR 125, and ECM 123 via one or more Analog to Digital Converters (ADC) 202 and Digital to Analog Converters (DAC) 203. The processor 121 can utilize computing technologies such as a microprocessor, Application Specific Integrated Chip (ASIC), and/or digital signal processor (DSP) with associated storage memory 208 such a Flash, ROM, RAM, SRAM, DRAM or other like technologies for controlling operations of the earpiece device 100. The processor 121 can also include a clock to record a time stamp.

The earpiece 100 can measure ambient sounds in the environment received at the ASM 111. Ambient sounds correspond to sounds within the environment such as the sound of traffic noise, street noise, conversation babble, or any other acoustic sound. Ambient sounds can also correspond to industrial sounds present in an industrial setting, such as, factory noise, lifting vehicles, automobiles, and robots to name a few.

Although the earpiece 100 when inserted in the ear can partially occlude the ear canal, the earpiece 100 may not completely attenuate the ambient sound. The passive aspect of the physical earpiece 100, due to the mechanical and sealing properties, can provide upwards of a 22 dB noise reduction. However, portions of ambient sounds higher than the noise reduction level can still pass through the earpiece 100 into the ear canal thereby producing residual sounds. For instance, high energy low frequency sounds may not be completely attenuated. Accordingly, residual sound may be resident in the ear canal and measured by the ECM 123.

The memory 208 can also store program instructions for execution on the processor 121 as well as captured audio processing data. For instance, memory 208 can be off-chip and external to the processor 121, and include a data buffer to temporarily capture the ambient sound and the internal sound, and a storage memory to save from the data buffer the recent portion of the history in a compressed format responsive to a directive by the processor 121. The data buffer can be a circular buffer that temporarily stores audio sound at a current time point to a previous time point. It should also be noted that the data buffer can in one configuration reside on the processor 121 to provide high speed data access. The storage memory can be non-volatile memory such as SRAM to store captured or compressed audio data.

The earpiece 100 can include an audio interface 212 operatively coupled to the processor 121 to receive audio content, for example from a media player or cell phone, and deliver the audio content to the processor 121. The processor 121 responsive to detecting events can adjust the audio content delivered to the ear canal. For instance, the processor 121 can lower a volume of the audio content responsive to detecting an event for transmitting the acute sound to the ear canal. The processor 121 by way of the ECM 123 can also actively monitor the sound exposure level inside the ear canal and adjust the audio to within a safe and subjectively optimized listening level range.

The earpiece 100 can further include a transceiver 204 that can support singly or in combination any number of wireless access technologies including without limitation Bluetooth™, Wireless Fidelity (WiFi), Worldwide Interoperability for Microwave Access (WiMAX), and/or other short or long range communication protocols. The transceiver 204 can also provide support for dynamic downloading over-the-air to the earpiece 100. It should be noted also that next generation access technologies can also be applied to the present disclosure.

The location receiver 232 can utilize common technology such as a common GPS (Global Positioning System) receiver that can intercept satellite signals and therefrom determine a location fix of the earpiece 100.

The power supply 210 can utilize common power management technologies such as replaceable batteries, supply regulation technologies, and charging system technologies for supplying energy to the components of the earpiece 100 and to facilitate portable applications. A motor (not shown) can be a single supply motor driver coupled to the power supply 210 to improve sensory input via haptic vibration. As an example, the processor 121 can direct the motor to vibrate responsive to an action, such as a detection of a warning sound or an incoming voice call.

The earpiece 100 can further represent a single operational device or a family of devices configured in a master-slave arrangement, for example, a mobile device and an earpiece. In the latter embodiment, the components of the earpiece 100 can be reused in different form factors for the master and slave devices.

Figure 3:
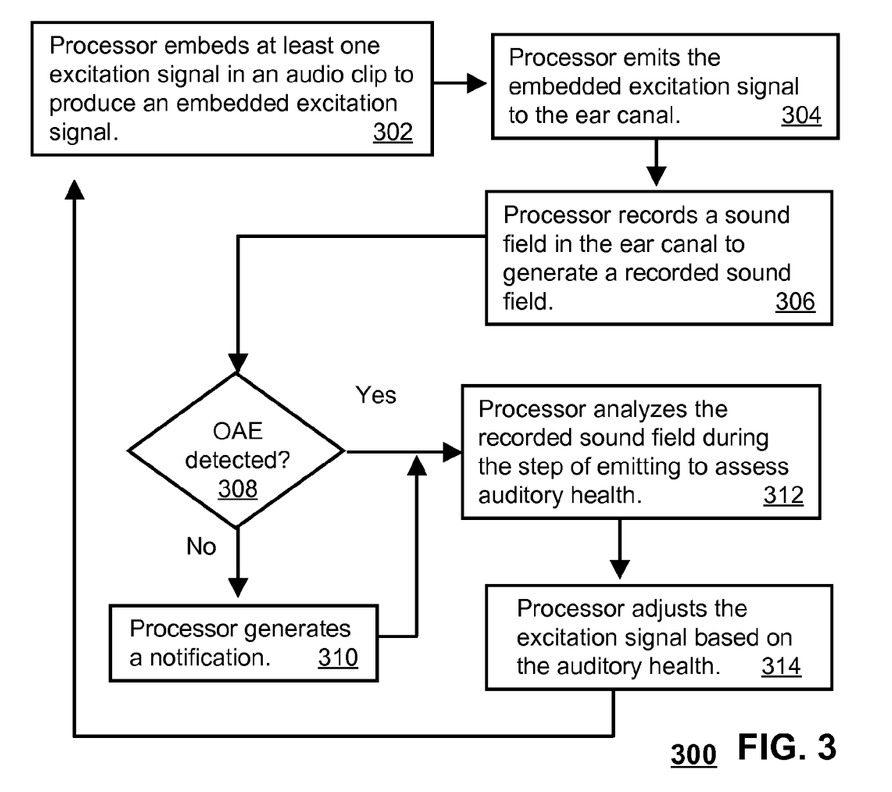
FIG. 3 is a flowchart of a method for evaluating auditory health using an embedded excitation signal in accordance with an exemplary embodiment.
Figure 4:
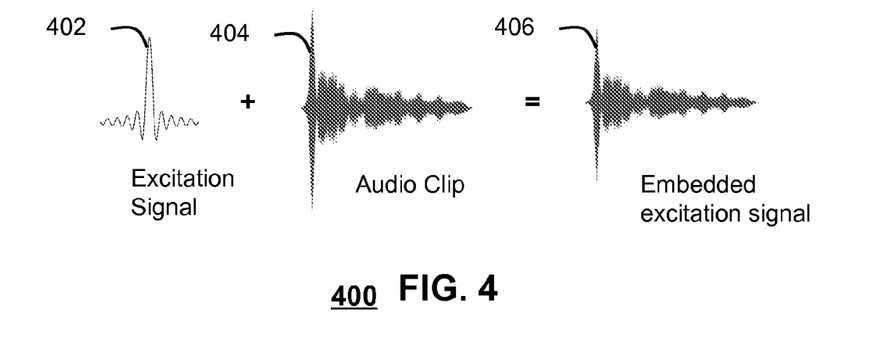
FIG. 4 is an illustration for mixing an excitation signal with an audio clip to produce an embedded excitation signal in accordance with an exemplary embodiment.

FIG. 3 is a flowchart of a method 300 for evaluating auditory health in accordance with an exemplary embodiment. The method 300 can be practiced with more or less than the number of steps shown and is not limited to the order shown. To describe the method 300, reference will be made to FIG. 4 and components of FIG. 1 and FIG. 2, although it is understood that the method 300 can be implemented in any other manner using other suitable components. The method 300 can be implemented in a single earpiece, a pair of earpieces, headphones, or other suitable headset audio delivery device.

The method 300 can start in a state wherein the earpiece 100 has been inserted and powered on. As shown in step 302, the processor 121 embeds at least one excitation signal 402 (see FIG. 4) in an audio clip 404 to produce an embedded excitation signal 406. The excitation signal 402 can be a single click, a sequence of clicks, one or more square wave pulses, one or more pulse shaped signals, one or more sinc functions, or a maximum length sequence (pseudo-random sequence). The audio clip 404 can be music, speech, or any other audible acoustic waveform. For instance, the audio clip 404 can be a portion of an MP3 song selected by the user, or a pre-recorded voice segment.

At step 304, the processor 121 emits the embedded excitation signal to the ear canal 131 via the ECR 125. The processor 121 can control the amplitude and timing of the embedded excitation signal as it is delivered to the ear canal 131. The embedded excitation signal can be approximately 35 dB-45 dB which allows an OAE response from the eardrum 133 to be detected even in loud ambient noise environments. Moreover, due to the sealing properties of the earpiece 100, the embedded excitation signal 406 is isolated within the ear canal cavity and can be radiated directly to the eardrum with minimal degradation due to the ambient sound environment.

At step 306, the processor 121 records a sound field in the ear canal 131 responsive to the step of emitting the embedded excitation signal 406 to the ear canal to generate a recorded sound field. The sound field generated in the ear canal 131 is a result of the embedded excitation signal impinging on the ear drum 133. Briefly, sympathetic nerves within the cochlea of the ear cause outer hair cells within the inner ear to generate a pressure on the basilar membrane supporting the outer hair cells which causes ossicles (middle ear bones) to resonate the eardrum 133 and emit a sound wave. The sound wave emitted by the ear drum 133 responsive to the embedded excitation signal generates the sound field within the ear canal 131. The sound field within the ear canal 131 thus contains sound frequencies characteristic of the cochlea's neuro-physiological cellular functions and accordingly the user's hearing health. The amplitude strength of the OAE can indicate the frequencies at which the user's hearing may be insensitive and/or degraded.

If at step 308, an OAE response from the ear drum is not detected, the processor 121 at step 310 generates a notification to the user. For instance, the earpiece 100 can generate an audible voice message to the user that the earpiece 100 is not receiving an OAE from the eardrum. This can be due to improper sealing of the earpiece 100 within the ear canal 131, or due to hearing insensitivity within the cochlea at certain frequencies. Not receiving an OAE response from the ear drum can be indicative of damaged hearing.

Figure 5:
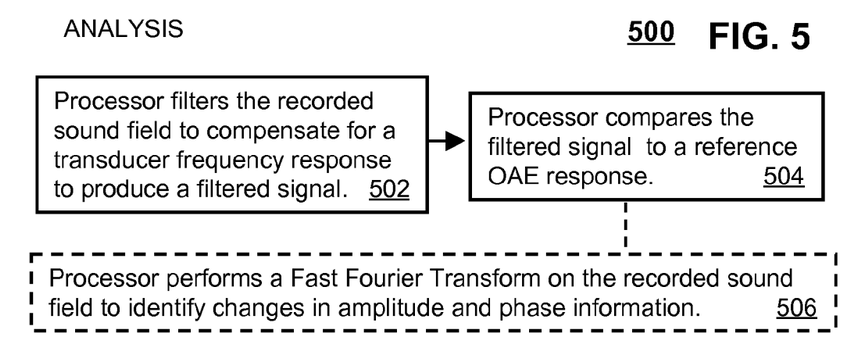
FIG. 5 is a method for analyzing a recorded sound field generated by an eardrum in accordance with an exemplary embodiment.

The method 300 can proceed to step 312 at which point the processor 121 analyzes the recorded sound field to assess auditory health. Notably, step 312 is also performed when an OAE response is conveyed by the ear drum 133 at step 308. (Briefly, FIG. 5 provides one embodiment 500 of step 312 for analyzing the sound field.) Otoacoustical emissions—corresponding to the OAE response—from hair cells of the inner ear resulting from the presentation of the excitation signal 402 to the ear canal can be analyzed and stored in the memory 208. The OAE responses can be used to identify previous exposure to very loud acoustic sound pressure levels capable of producing short term hearing threshold shifts, in addition to permanent loss in hearing over time.

At step 314, the processor 121 adjusts the excitation signal based on the auditory health. The processor adjusts the excitation signal 402 in a particular manner to further investigate the differences elucidated in step 312 between the filtered signal ((see 504, FIG. 5, individual OAE response) and the reference OAE response (average OAE group response) that indicates the health of the cochlea). (Briefly, FIG. 6 provides one embodiment 600 of step 314 for adjusting the excitation signal.)

Upon the completion of step 314, the method 300 can return to step 302 to repeat the personalized hearing test. In such regard, the processor 121 can continually adapt the excitation signal 402 for mixing with the audio clip 404 in real-time as the embedded excitation signal 406 is presented to the user. Notably, the processor 121 upon analyzing the OAE responses generated by the eardrum with respect to knowledge of the frequency components of the embedded excitation signal 406 adjusted over time, can assess the user's hearing health.

Referring to FIG. 5, one embodiment 500 for analyzing the sound field is provided in accordance with step 312 of method 300. As shown at step 502, the processor 121 can filter the recorded sound field to compensate for a transducer frequency response to produce a filtered signal. In particular, the sound field frequency response can be equalized to account for the effects of the ECR 125 and ECM 123. At step 504, the processor 121 can compare the filtered signal to a reference OAE response. The reference OAE response can be a generic OAE response averaged for a large number of individuals. The memory 208 can store one or more reference OAE responses for comparison against the filtered signal. The comparison of the filtered signal with the reference OAE response reveals portions of the frequency spectrum where the immediate user (filtered signal) differs in hearing health (e.g., clinical, physiological, neuron-physiological, acuity) with respect to a general population of healthy hearing individuals. For example, at step 506, the processor 121 can optionally perform a Fast Fourier Transform (FFT) on the recorded sound field to identify changes in amplitude and phase information.

Figure 6:
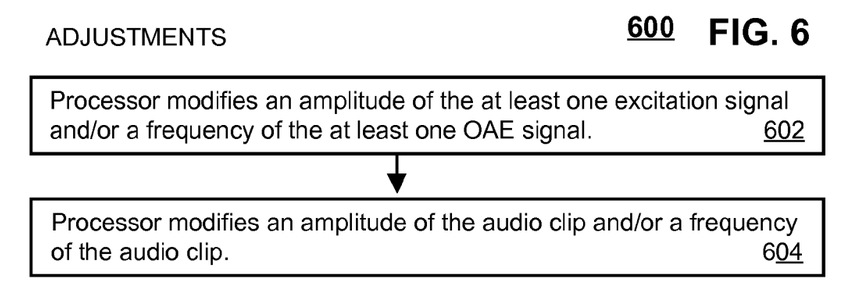
FIG. 6 is a method for adjusting an excitation signal in accordance with an exemplary embodiment.

Referring to FIG. 6, one embodiment 600 for analyzing the sound field is provided in accordance with step 314 of method 300. As shown at step 602, the processor 121 modifies at least one among an amplitude of the at least one excitation signal 402 and a frequency of the at least one excitation signal 402. For instance, the processor 121 can time disperse the excitation signal 402 to alter the frequency resolution and amplitude of the excitation signal. Alternatively, or in addition to, the processor 121 at step 604 modifies at least one among an amplitude of the audio clip and a frequency of the audio clip. For instance, the processor 121 can adjust the placement (time positioning) of the excitation signal 402 within the audio clip 404. The excitation signal 402 can be placed during brief pauses, silence intervals, or null frequency regions with respect to the frequency content of the excitation signal.

Figure 7:
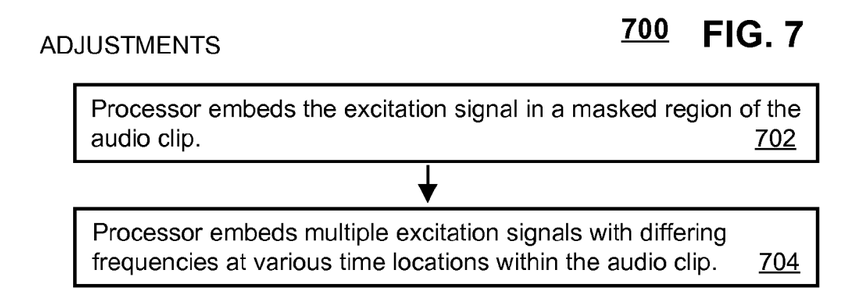
FIG. 7 is another method for adjusting an excitation signal in accordance with an exemplary embodiment.

For example as shown in the embodiment 700 in FIG. 7, the processor 121 can embed the excitation signal 402 in a masked region of the audio clip 404 as shown in step 702. A masked region corresponds to an inaudible region of the audio clip that is not audibly perceived by the user. In such regard, the presentation of the embedded excitation signal, with respect to hearing sensitivity, sounds like the original audio clip 404. That is, the user does not audibly perceive the presence of the excitation signal within the audio clip 404. Further, as shown in step 704, the processor 121 can embed multiple excitation signals with differing frequencies and durations at various time locations within the audio. By way of the ECM 123, the processor 121 can evaluate the frequency content (and also masking properties) of the audio signal prior to inserting the excitation signal. In addition to implementing predictive processing techniques, the processor 121 has knowledge of forthcoming audio clip 404 samples which are retrieved from memory 208 (sound library). This allows the processor 121 to intelligently identify portions of the audio clip that can be supplemented with the excitation signal 402 without modifying the perceived audio content.

Figure 8:
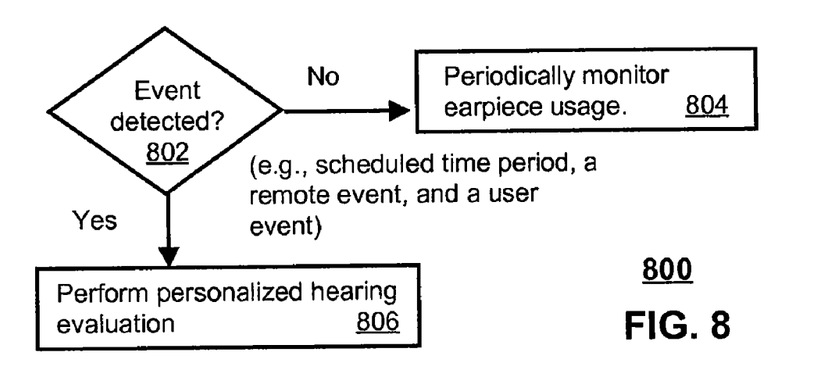
FIG. 8 is a state diagram for initiating an auditory hearing evaluation responsive to an event in accordance with an exemplary embodiment.

FIG. 8 is state diagram 800 for initiating an auditory hearing test responsive to an event in accordance with an exemplary embodiment. The state diagram 800 can be practiced with more or less than the number of states shown and is not limited to the order shown. The auditory hearing test can be a personalized hearing evaluation based on hearing profiles of the individual users.

As shown in state 802, the earpiece can trigger a hearing test in response to detecting an event. The event can be a scheduled time period, a remote event, or a user event. A remote event can be scheduled by a service provider to evaluate the user's hearing. A user event can be generated by the user, for example, a touching of the earpiece 100. For instance, the user can touch the earpiece 100 to start a personalized hearing test based on OAE measurements. If an event is detected, the earpiece 100 can proceed to perform the personalized hearing evaluation at state 806. In particular, responsive to the event, the earpiece 100 can record the sound field in the ear canal to generate the recorded sound field. This sound field can be further analyzed to assess auditory health and adjust the excitation signal as previously described in method 300. If an event is not detected, the earpiece 100 can periodically monitor earpiece usage 100 as shown in step 804. For instance, the earpiece 100 can assess sound exposure level over time (ambient sound, audio content, internal sound level) and chart the exposure level for scheduling the personalized hearing evaluation.

Briefly, the personalized hearing evaluation can test the user's hearing in a non-intrusive and convenient manner based on analysis of OAE responses. As previously noted, the excitation signal 402 can be embedded within the audio clip 404 so as not to be audibly perceived by the user. In such regard, multiple excitation signals can be embedded within an audio clip to test the user's hearing such that they are not aware or annoyed by the hearing test. The hearing test that is conducted in response to detecting the event includes aspects of method 300, including, embedding the excitation signal in the audio clip to produce the embedded excitation signal, emitting the embedded excitation signal to the ear canal, recording a sound field in the ear canal to generate the recorded sound field, analyzing the recorded sound field to assess auditory health, and adjusting the excitation signal based on the auditory health.

Figure 9:
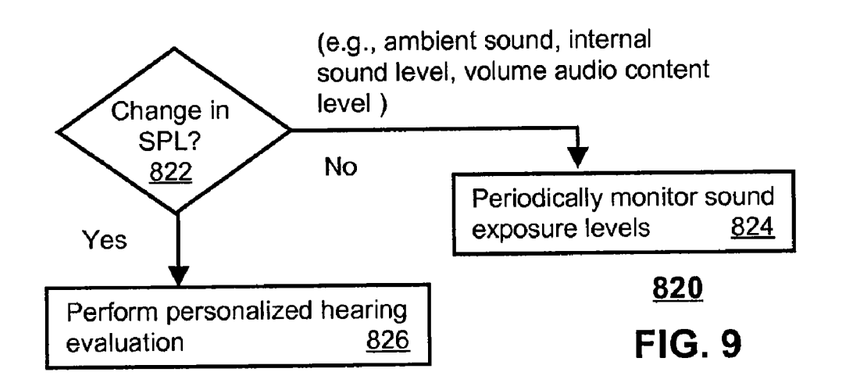
FIG. 9 is a state diagram for initiating an auditory hearing evaluation responsive to a change in level in accordance with an exemplary embodiment.

FIG. 9 is state diagram 820 for initiating an auditory hearing evaluation responsive to a change in level in accordance with an exemplary embodiment. The state diagram 820 can be practiced with more or less than the number of states shown and is not limited to the order shown.

As shown in state 822, the earpiece 100 can trigger a personalized hearing evaluation at step 826 in response to detecting a change in sound pressure level (SPL). The level may be associated with an external sound measured by the ASM 111, an internal sound measured by the ECM 123, or any other sound level. The change in SPL can also be due to volume level adjustment of audio content delivered to the ear canal via the ECR 125. The earpiece 100 can record the sound field in the ear canal responsive to detecting a level change, such as a volume increase of audio content presented to the ear canal. If a change in SPL is not detected, the earpiece can proceed to state 824 to periodically monitor sound exposure levels, for example, from the ASM 111, ECM 123, and ECR 125.

Figure 10:
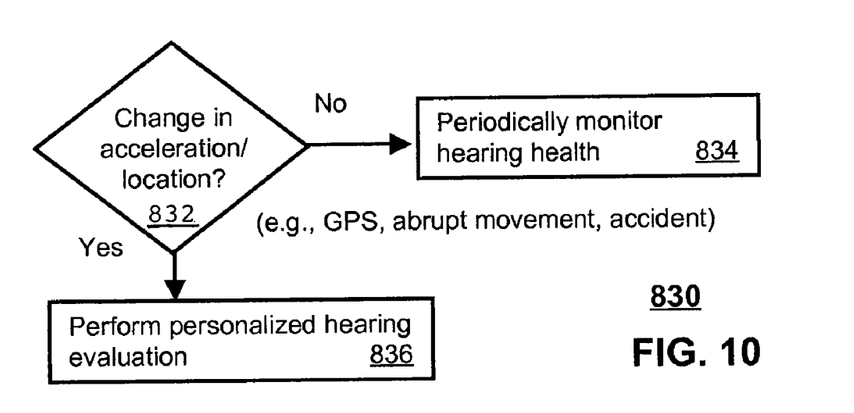
FIG. 10 is a state diagram for initiating an auditory hearing evaluation responsive to a change in acceleration or location in accordance with an exemplary embodiment.

FIG. 10 is state diagram 830 for initiating an auditory hearing evaluation responsive to a change in acceleration or location in accordance with an exemplary embodiment. The state diagram 830 can be practiced with more or less than the number of states shown and is not limited to the order shown.

As shown in state 832, the earpiece 100 can trigger a personalized hearing evaluation at step 836 in response to detecting a change in acceleration or location. A change in acceleration may be due to the user falling down, an accident, or the earpiece receiving a jarred motion (such as falling from the ear). Accordingly, the earpiece 100 can perform the personalized hearing test to determine if the earpiece 100 is properly inserted, absent from the ear canal, or if the user is attentive. A change in location may be due to the user moving to a different location in a factory. Accordingly, a personalized hearing test can be triggered when the user moves to other locations. The earpiece can assess how long a user has been at a location before triggering the hearing test. The earpiece by way of the location receiver 232 can provide a position of the user (e.g., latitude, longitude, elevation) for making the determination at step 832. If a change in acceleration or location is not detected, the earpiece can proceed to state 834 to periodically monitor the user's hearing health.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. A method for evaluating an auditory health of a subject, the method comprising:
    embedding at least one excitation signal in an audio clip to produce an embedded excitation signal, the audio clip not being associated with the at least one excitation signal;
    emitting the embedded excitation signal to an ear canal of the subject;
    recording a sound field in the ear canal responsive to the step of emitting the embedded excitation signal to the ear canal to generate a recorded sound field; and
    analyzing the recorded sound field to evaluate the auditory health of the subject.

2. The method of claim 1, wherein the sound field includes an otoacoustic emission from an eardrum of the subject and audio content from the audio clip.

3. The method of claim 1, wherein the excitation signal is at least one among a click, a pulse, or a sinc function.

4. The method of claim 1, wherein the audio clip includes at least one among tones, music and speech.

5. The method of claim 1, further comprising embedding the at least one excitation signal in a masked region of the audio clip.

6. The method of claim 1, further comprising embedding multiple excitation signals with differing frequencies at various time locations within the audio clip.

7. The method of claim 1, further comprising:
    adjusting the embedded excitation signal based on the auditory health evaluated responsive to the analyzing of the recorded sound field.

8. The method of claim 1, further comprising performing a Fast Fourier Transform on the recorded sound field to identify changes in amplitude and phase information.

9. The method of claim 1, wherein the ear canal is at least partially occluded by an earpiece,
    the analyzing of the recorded sound field includes analyzing the recorded sound field within the ear canal during continuous delivery of the embedded excitation signal to evaluate the auditory health, the method further comprising:
    adjusting a mixing of the at least one excitation signal with the audio clip during the emitting based on comparative differences of the recorded sound field with a reference otoacoustic emission (OAE).

10. The method of claim 1 further comprising:
    embedding the at least one excitation signal in the audio clip responsive to detecting a change in an internal sound level within the ear canal, the ear canal being at least partially occluded by an earpiece.

11. The method of claim 1, further comprising, responsive to an event, recording the sound field in the ear canal to generate the recorded sound field, wherein the event is at least one among a scheduled time period, a remote event, and a user event.

12. The method of claim 1, further comprising, responsive to an event, recording the sound field in the ear canal to generate the recorded sound field, wherein the event is a change in a location or a change in an acceleration.

13. The method of claim 1, further comprising recording the sound field in the ear canal responsive to detecting a volume increase of audio content presented to the ear canal.

14. The method of claim 1, further comprising:
responsive to an event, analyzing the recorded sound field to evaluate the auditory health; and
adjusting the excitation signal based on the auditory health.

15. The method of claim 7, wherein the step of adjusting the embedded excitation signal further comprises modifying an amplitude and a frequency of the audio clip.

16. The method of claim 1, wherein the step of analyzing further comprises:
filtering the recorded sound field to compensate for a transducer frequency response to produce a filtered signal; and
comparing the filtered signal to a reference otoacoustic emission (OAE) response.

17. The method of claim 7, wherein the step of adjusting the embedded excitation signal further comprises modifying an amplitude and a frequency of the at least one excitation signal.

18. An earpiece at least partially occluding an ear canal, comprising:
an Ear Canal Receiver (ECR) to deliver audio to the ear canal;
an Ear Canal Microphone (ECM) to capture internal sound in the ear canal;
a processor operatively coupled to the ECR and ECM to
embed at least one excitation signal in an audio clip to produce an embedded excitation signal, the audio clip not being associated with the at least one excitation signal;
emit the embedded excitation signal to the ear canal via the ECR; and
record a sound field in the ear canal via the ECM responsive to the emitted signal to generate a recorded sound field; and
a memory to store the recorded sound field.

19. The earpiece of claim 18, further comprising:
an Ambient Sound Microphone (ASM) to capture ambient sound in an environment, wherein the processor records the ambient sound and the sound field.

20. The earpiece of claim 18, wherein the processor detects a change in an internal sound level and embeds at least one more excitation signal in the audio clip responsive to detecting the change.

21. The earpiece of claim 18, wherein the processor:
analyzes the recorded sound field to assess an auditory health of a subject responsive to an event, and
adjusts the embedded excitation signal based on the auditory health.

22. A system for monitoring an auditory health of a subject, the system comprising:
an earpiece comprising:
an Ear Canal Receiver (ECR) to deliver audio to an ear canal of the subject;
an Ear Canal Microphone (ECM) to capture internal sound in the ear canal; and
a transceiver operatively coupled to the ECR and the ECM to transmit and receive the audio and the internal sound, and
a remote processor communicatively coupled and external to the earpiece to:
embed at least one excitation signal in an audio clip to produce an embedded excitation signal, the audio clip not being associated with the at least one excitation signal;
emit the embedded excitation signal to the ear canal using the ECR via the transceiver; and
record a sound field in the ear canal using the ECM via the transceiver responsive to the emitted signal to generate a recorded sound field; and
a memory to store the recorded sound field,
wherein the transceiver transmits and sends data in a compressed format over at least one among a wired or wireless communication channel.

23. The system of claim 22, wherein the remote processor analyzes the recorded sound field to assess the auditory health of the subject responsive to an event; and
adjusts the embedded excitation signal based on the auditory health.

24. The system of claim 22, wherein the remote processor schedules the emitting of the embedded excitation signal responsive to detecting a change in a location of the earpiece, or a change in an acceleration of the earpiece.

25. The system of claim 22, wherein the remote processor embeds the at least one excitation signal in a masked region of the audio clip.

* * * * *